US00PP16815P3

(12) United States Plant Patent
Hawkersmith

(10) Patent No.: US PP16,815 P3
(45) Date of Patent: Jul. 11, 2006

(54) SUGAR MAPLE NAMED 'HAWKERSMITH 1'

(50) Latin Name: *Acer saccharum*
Varietal Denomination: Hawkersmith 1

(75) Inventor: Louis A. Hawkersmith, Tullahoma, TN (US)

(73) Assignee: Heartland Nursery Company, New Madrid, MO (US)

( * ) Notice: Subject to any disclaimer, the term of this patent is extended or adjusted under 35 U.S.C. 154(b) by 0 days.

(21) Appl. No.: 10/230,453

(22) Filed: Aug. 29, 2002

(65) Prior Publication Data

US 2004/0045062 P1 Mar. 4, 2004

(51) Int. Cl.
*A01H 5/00* (2006.01)

(52) U.S. Cl. ..... Plt./224

(58) Field of Classification Search ..... Plt./224
See application file for complete search history.

*Primary Examiner*—Kent Bell
(74) *Attorney, Agent, or Firm*—Polster, Leider, Woodruf & Lucchesi, L.C.

(57) ABSTRACT

A new culivar of Sugar Maple tree (*Acer saccharum*) having a compact oval appearance, dark red to bronze new growth and fall foliage, small, dark and slightly thicker leaves, good summer heat and drought resistance and cold hardiness. The tree is beautiful, compact, tought, colorful and functional as an ornamental shade tree.

6 Drawing Sheets

Genus and species:
The present plant is a variety of *Acer saccharum* and its cultivar denomination is 'Hawkersmith 1'.

BACKGROUND OF THE INVENTION

The present invention relates to a new and distinct variety of Sugar Maple tree which I have named 'Hawkersmith 1'.

The original Sugar Maple tree of the new cultivar was selected in 1985 from a block of seedlings planted in rows in a production field in Tullahoma, Tenn. The seedlings were planted in rows and designed to be sold at a caliper of 4–10 inches. The selection was made on the basis of the distinctive characteristics of a single tree (as hereinafter described) noted after a few years of growth. The new cultivar was growing in a seedling block of standard *Acer saccharum* trees. The seed source is unknown and the origin of the seedlings is unknown. The present seedling was selected from the others in the block because it was smaller and more thickly branched. Its leaf color was dull and the leaves were smaller than the other seedlings. Its fall color was more red to burgundy and the other seedlings were more yellow to orange.

The new cultivar has been asexually reproduced successfully by chip budding onto *Acer saccharum* rootstock at New Madrid, Mo.

It has been found that the new *Acer saccharum* cultivar exhibits the following combination of characteristics.

1. A much smaller leaf than other Sugar Maples.
2. A slightly darker leaf than other Sugar Maples.
3. A slightly thicker leaf than other Sugar Maples based on feel and appearance, although the precise thickness has not been measured.
4. In full leaf, the branching structure has a layered appearance.
5. When dormant and in full leaf, the Sugar Maple looks as if it has been sheared (very dense branching).
6. The new growth is dark red to bronze.

7. The fall color is very similar to new growth.
8. The tree is almost semi-dwarf.
9. The rate of growth is moderate when young and very slow after 10 years.
10. The bark is gray.
11. The tree is very tolerant to summer heat of the south.
12. The tree has no winter die back and is very cold hardy.
13. The color of new growth and fall color seem to be consistent from year to year.
14. The leaves turn fall color 2–3 weeks later than other Sugar Maples.

Comparable cultivars include 'Green Mountain' sugar maple Pat. No. 2,339. Compared to 'Green Mountain', the present cultivar is semi-dwarf having smaller, thinner leaves than 'Green Mountain'. It requires minimal pruning, is slower growing and the leaves are dull and not glossy. In the fall the leaves of the instant tree are a red to burgundy color whereas 'Green Mountain' is more orange to yellow in color.

Compared to 'Legacy' sugar maple, the leaves of the instant cultivar are thinner and duller in appearance. 'Legacy' has glossy waxy leaves. 'Legacy' is a large full growing tree whereas the instant cultivar is semi-dwarf and requires little pruning. The full coloration of the instant cultivar is red to burgundy and 'Legacy' is yellow-orange.

The tree characteristics following asexual reproduction are the same as those of the original tree of the new cultivar. The tree has shown no winter die back and is cold hardy. It also is very tolerant of southern summer heat and is more drought tolerant compared to other Sugar Maples grown under the same circumstances.

The new cultivar of the present invention has been named the 'Hawkersmith 1' cultivar and is being marketed under the AUTUMN FAITH trademark.

DESCRIPTION OF THE PHOTOGRAPHS

The accompanying photographs show, as nearly true as is reasonably possible to make the same in color illustrations of this character, typical specimens and plant parts of the new cultivar. The tree depicted in the photograph is growing in Tullahoma, Tenn.

FIG. 1 illustrates during the month of July a mature tree of the new cultivar at an age of approximately 20 years. The trunk diameter is about 8 inches measured 4 feet from the base, the height is about 25 feet and the maximum breadth is approximately 15 feet.

DETAILED DESCRIPTION

Figure 1:
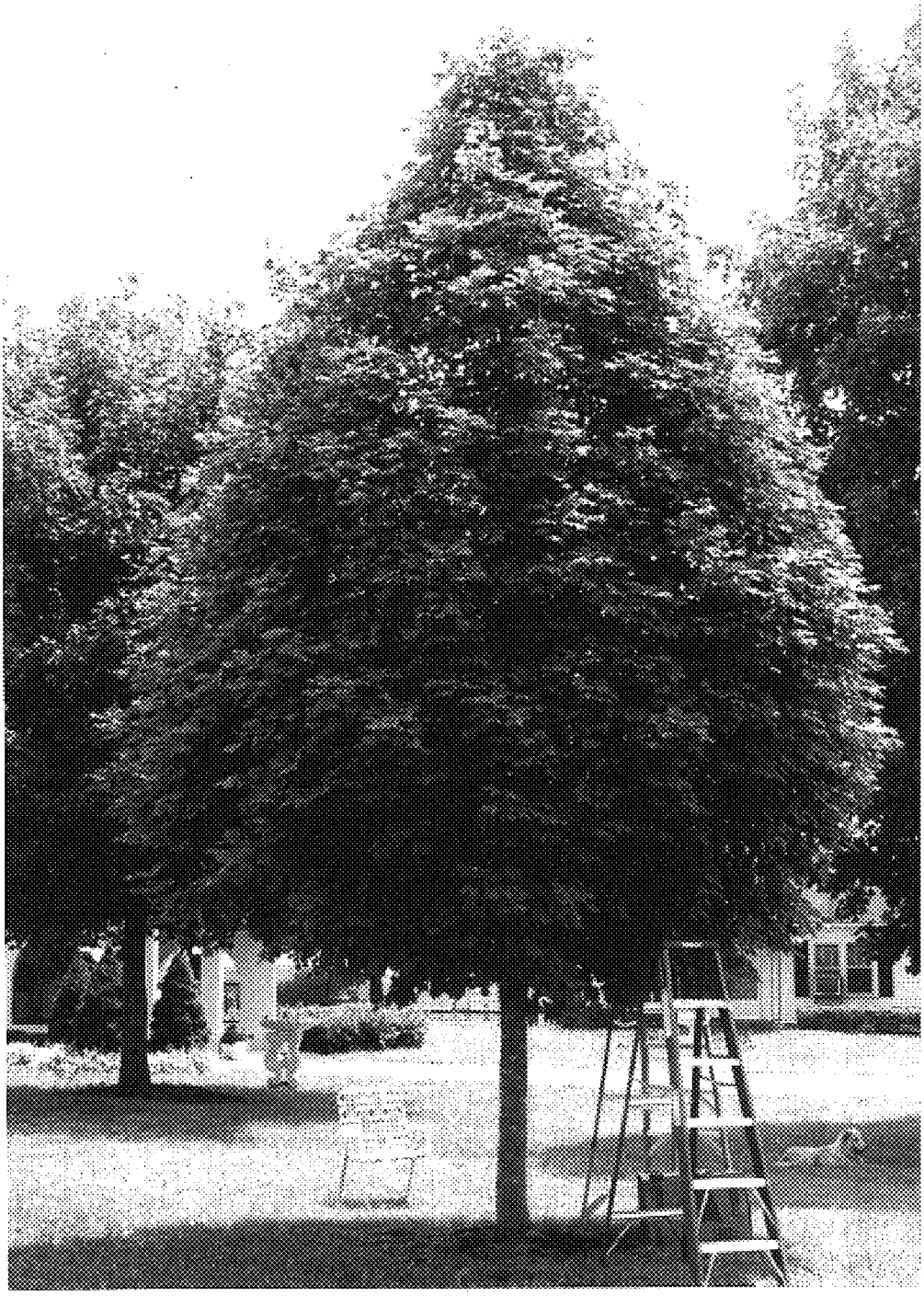
Figure 2:
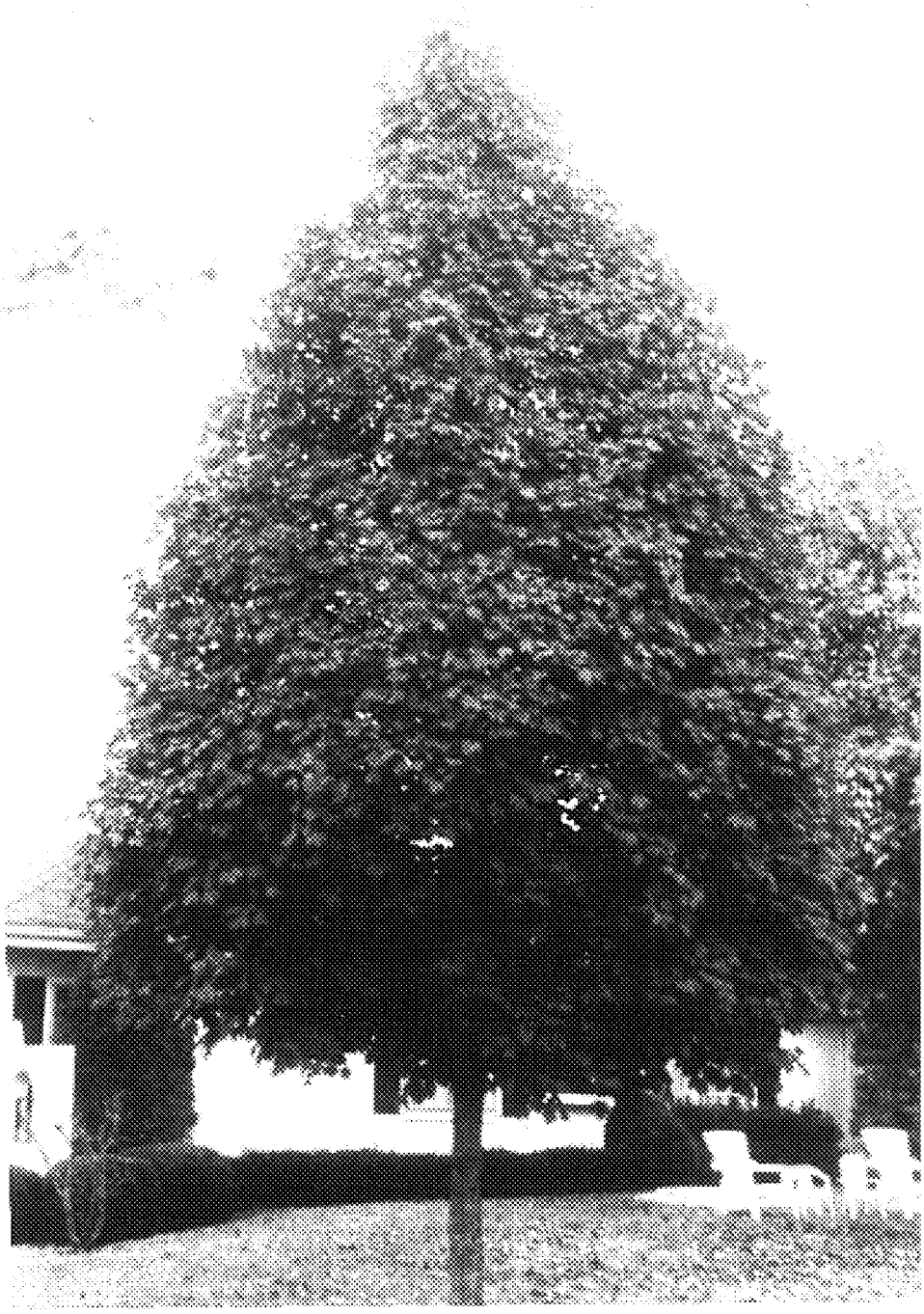
FIG. 2 illustrates the 20 year old tree of FIG. 1 during the month of November. Fall coloration in shades of dark red and bronze is apparent.
Figure 3:
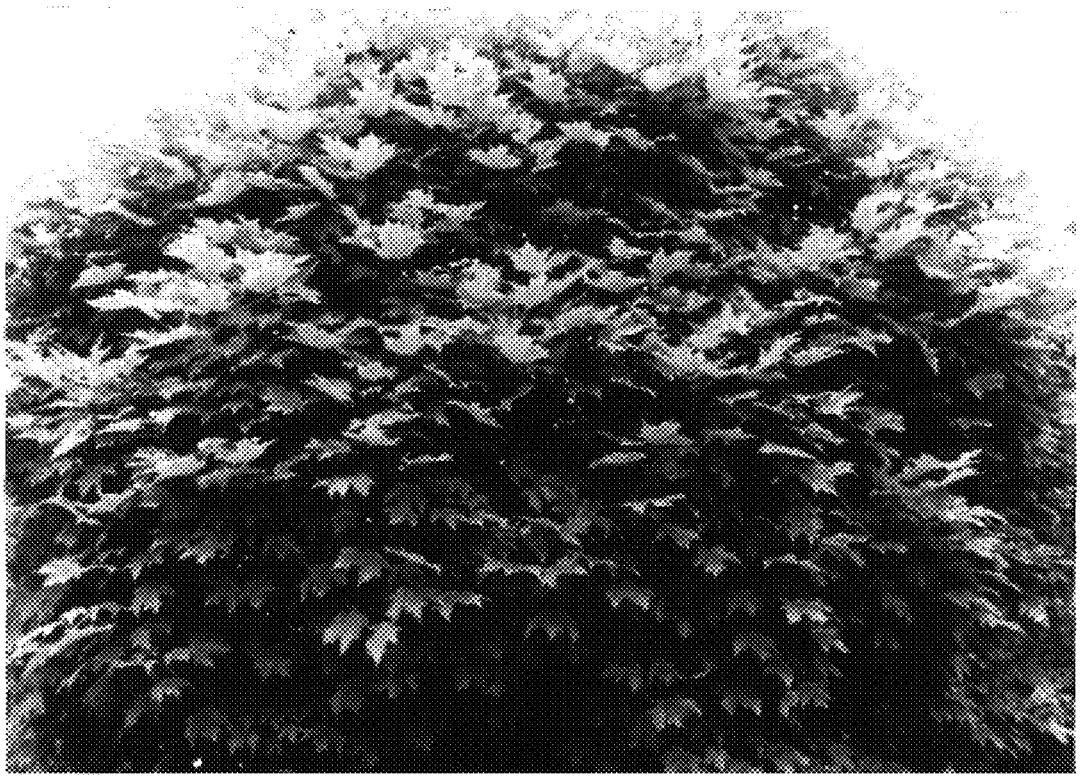
FIG. 3 shows a close-up of the dense summer foliage of the 20 year old tree of FIG. 1.
Figure 4:
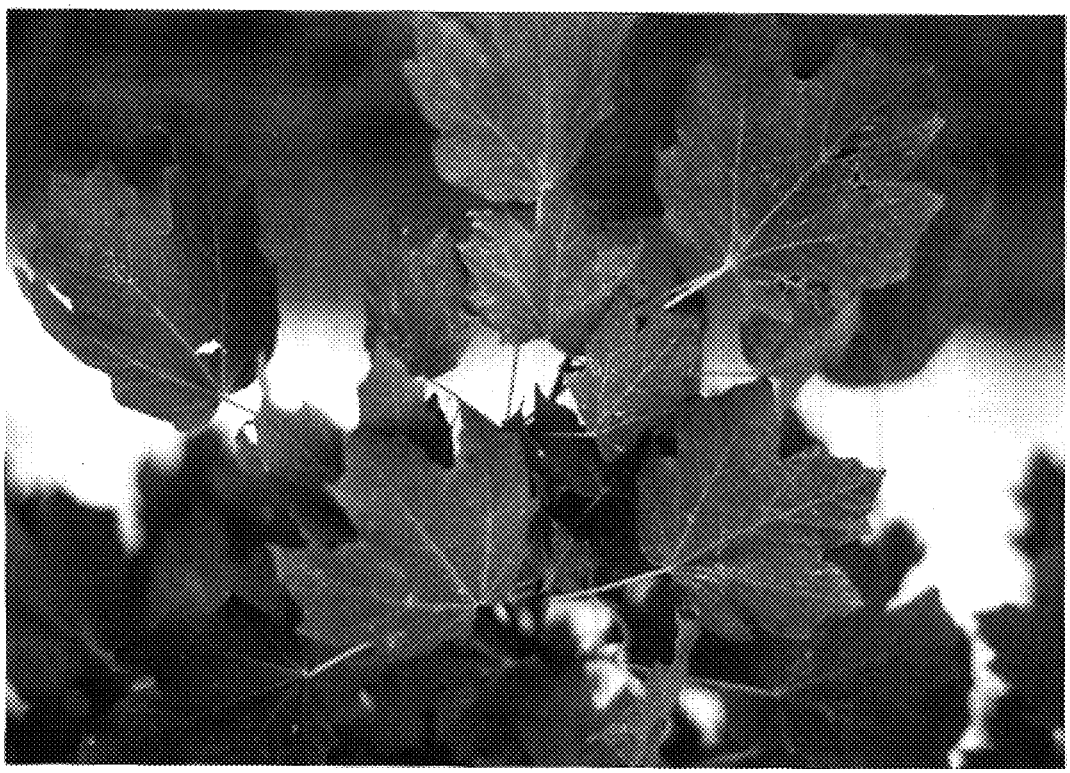
FIG. 4 is a close-up of individual leaves showing the smaller darker mature leaf of the 20 year old tree.
Figure 5:
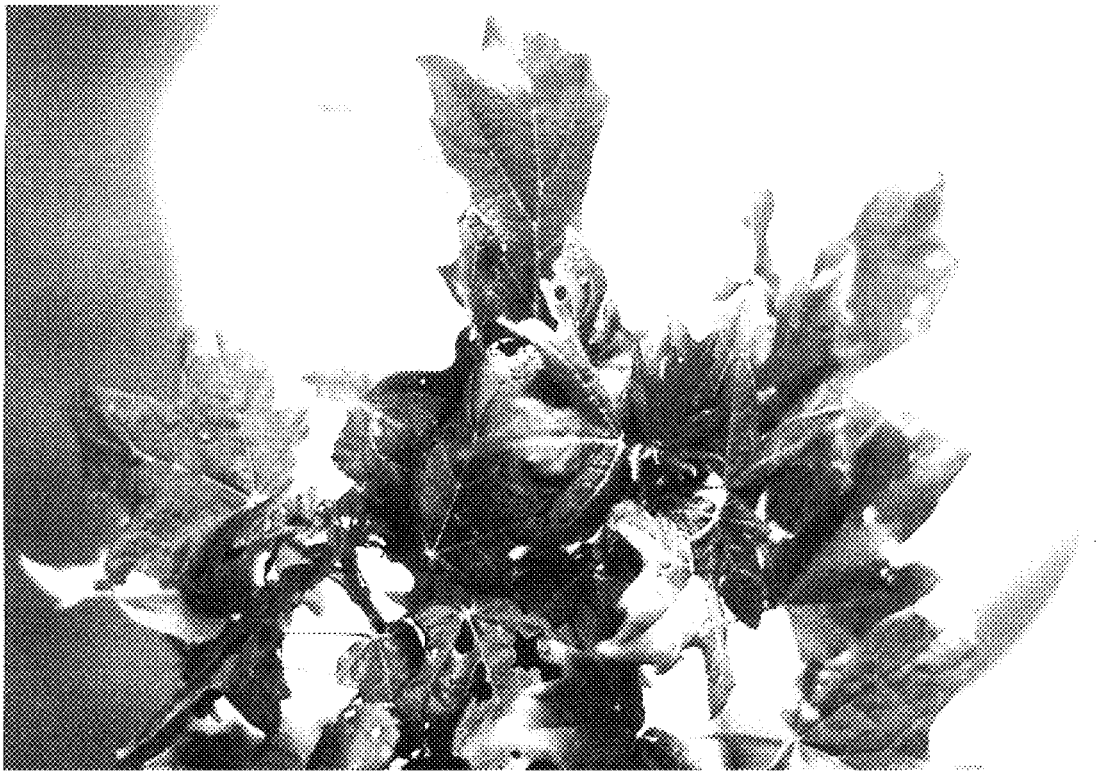
FIG. 5 shows the new leaf growth of the 20 year old tree during the month of May in shades of dark red and bronze.
Figure 6:
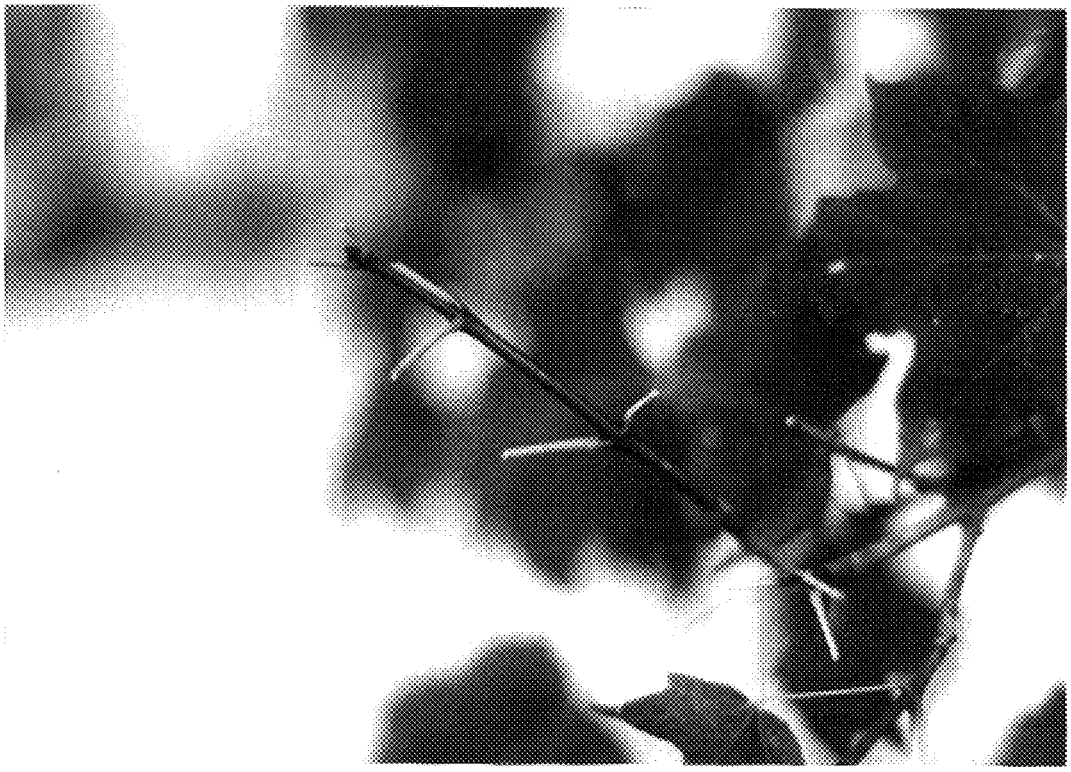
FIG. 6 shows the gray bark and the bud sets varying from ¼ inch at the ends of the branch to 2 inches apart toward the center of the 20 year old tree.

The following is a detailed description of my new variety of Sugar Maple. The chart used in identification of colors is that of The Royal Horticultural Society (R.H.S. Colour Chart). Common color terms are to be accorded their ordinary dictionary meaning. The description is based on a test planting of the new variety at New Madrid, Mo. and on the 20 year old tree shown in the photographs.

Parentage: Chance seeding of *Acer saccharum* of unknown origin found growing in a cultivated area in Tullahoma, Tenn. The seedling was notably shorter and had smaller leaves than the other seedlings around it.

Tree shape: Upright, oval with layered very dense branch structure.

Size: Smaller than standard *Acer saccharum* of same age; almost semi-dwarf. The height is almost 25 feet and breadth is about 15 feet at 20 years. The mature size should be no more than 35 feet.

Growth: Moderate when young; very slow after 10 years.

Trunk: Generally straight and upright and trunk diameter is 8 inches measured 4 feet from the base.

Bark: Gray Group 201C, Fan 4 Grey (R.H.S.).

Branches: On a typical sugar maple measuring the same height as 'Hawkersmith 1', a branch measured 8 feet from ground level was 5½ inches in caliper measured 6 inches from main trunk and was 15 feet in length. Texture is smooth and coloration was found to match Fan 4 page 200 A Brown Group (R.H.S.). 'Hawkersmith 1' has a branch caliper of 2⅛ inches and a length of 8 feet, 4 inches, both being measured by the same specifications as was the typical sugar maple. Texture is smooth and coloration matches Fan 4, page 199 B Grey/Brown Group (R.H.S.).

Leaves: Much smaller, slightly darker and slightly thicker than standard Sugar Maple. On a typical sugar maple the leaf shape is simple and palmate. The length is 3 inches, the width is 6 inches, the apex is acuminate, the base is cordate, and the margin is lobed. 'Hawkersmith1' leaf shape is simple and palmate. The length is from 2 1/16 inches to 4 1/16 inches. The width is from 2⅜ inches to 4 15/16 inches. The apex is acuminate, the base is cordate, and the margin is lobed. Visually the leaf is heavier and thicker as can be noted in the photos.

Color: The new growth and fall color of the leaves of the instant tree is dark red to bronze. The summer color is darker green than standard *Acer saccharum*. The leaves turn their fall color 2–3 weeks later than standard Sugar Maples.

Bud sets: Vary from ¼" apart at the ends of the branches to about 2" apart toward the trunk. The buds are brown and scaly. The bud shape is conical ⅛ inch long, 1/16 inch wide and the color was found to match Fan 4, page 200 C, Brown Group (R.H.S.).

Reproductive organs and fruit: No seed, fruit or flowers have yet been observed.

Petiole: The petiole length is from 1⅜ inches to 5⅜ inches. The diameter is from 1/32 inch to 1/16 inch.

Ability to withstand head: The tree is tolerant of summer heat in the South and is very drought tolerant compared to standard Sugar Maple.

Cold hardiness: The tree has no winter die back. It also has withstood high winds and ice in USDA Zones 4–8.

Disease resistance: No disease or insect problems have been noted.

Leaf and petiole color comparison with The Royal Horticultural Society Colour Chart: New Petiole — Fan 3 Yellow - Green group 146 B. New Leaf Upper Surface — Fan 4 Greyed - Purple group 185 B. New Leaf Lower Surface — Fan 4 Greyed - Purple group 186 C. Summer Petiole — Fan 3 Yellow - Green group N 144 D. Summer Leaf Upper Surface — Fan 3 Yellow - Green group 147 A. Summer Leaf Lower Surface — Fan 3 Yellow - Green group 144 A. Fall Petiole — Fan 4 Greyed - Green group 197 C. Fall Leaf Upper Surface — Fan 4 Greyed - Purple group 184 C. Fall Leaf Lower Surface — Fan 4 Greyed - Purple group 185 D.

What is claimed:

1. A new and distinct variety of Sugar Maple tree substantially as herein shown and described, characterized particularly as to novelty by a compact shape, moderate to slow growth, small, dark and somewhat thicker leaves, good drought and summer heat resistance, resistance to wind and cold, and new growth and fall coloration being dark red to bronze.

* * * * *